United States Patent
Morrison

(10) Patent No.: US 12,064,093 B2
(45) Date of Patent: Aug. 20, 2024

(54) CLEANING INDICATOR AND METHOD OF USING SAME

(71) Applicant: Advanced Sterilization Products, Inc., Irvine, CA (US)

(72) Inventor: Todd Morrison, Dana Point, CA (US)

(73) Assignee: Advanced Sterilization Products, Inc., Irvine, CA (US)

( * ) Notice: Subject to any disclaimer, the term of this patent is extended or adjusted under 35 U.S.C. 154(b) by 91 days.

(21) Appl. No.: 17/440,142

(22) PCT Filed: Mar. 19, 2020

(86) PCT No.: PCT/IB2020/052550
§ 371 (c)(1),
(2) Date: Sep. 16, 2021

(87) PCT Pub. No.: WO2020/194148
PCT Pub. Date: Oct. 1, 2020

(65) Prior Publication Data
US 2022/0151477 A1 May 19, 2022

Related U.S. Application Data

(60) Provisional application No. 62/822,179, filed on Mar. 22, 2019.

(51) Int. Cl.
*A61B 1/12* (2006.01)
*A61B 90/70* (2016.01)
(Continued)

(52) U.S. Cl.
CPC .............. *A61B 1/123* (2013.01); *A61B 90/70* (2016.02); *G01N 21/94* (2013.01);
(Continued)

(58) Field of Classification Search
None
See application file for complete search history.

(56) References Cited

U.S. PATENT DOCUMENTS 5,206,118 A 4/1993 Sidney et al.
6,485,979 B1 11/2002 Kippenhan et al.
(Continued)

FOREIGN PATENT DOCUMENTS

DE 102010033016 A1 * 2/2012 ............. A61B 90/70
DE 102016107040 * 10/2017 ............. A61B 90/70
(Continued)

OTHER PUBLICATIONS

"CDWA Cleaning Indicator Rev.12", Terragene, Jul. 2017, Accessed on Feb. 2023. Retrieved from: https://scu.com.tr/wp-content/uploads/2017/08/CDWA-Rev.12.pdf (Year: 2017).*
JP2006346136 English translation, accessed on Apr. 2023. (Year: 2006).*
DE102010033016 English translation, accessed on Apr. 2023. (Year: 2012).*
DE102016107040 English translation, accessed on Apr. 2023. (Year: 2017).*
JP2009061012 English translation, accessed on Apr. 2023. (Year: 2009).*

(Continued)

*Primary Examiner* — Eric W Golightly
*Assistant Examiner* — Arlyn I Rivera-Cordero
(74) *Attorney, Agent, or Firm* — Lerner David LLP

(57) ABSTRACT

A cleaning indicator including a substrate having an image upon it that can be interrogated to assist in monitoring a process for washing articles in a washing machine system. The image can be a printed image, which in turn is covered at least partially by a test soil to be removed by the washing process. Alternatively, the test soil can be formed into an image on the substrate. The cleaning indicator can be imaged before the start of a washing process to allow the washing process to proceed only if the appropriate image is observed. The cleaning indicator can be imaged during operation of the washing process, and when a criterion for cleanliness is met, the washing process can be automatically terminated. A washing system for using the cleaning indicator in an automated washing process is also disclosed.

8 Claims, 7 Drawing Sheets

(51) Int. Cl.
*B08B 3/04* (2006.01)
*G01N 21/94* (2006.01)

(52) U.S. Cl.
CPC ... *A61B 2090/701* (2016.02); *A61B 2090/702* (2016.02); *B08B 3/04* (2013.01)

(56) References Cited

U.S. PATENT DOCUMENTS

| | | | |
|---|---|---|---|
| 6,555,826 | B2 | 4/2003 | Hoffmann |
| 7,263,220 | B2 | 8/2007 | Crandall et al. |
| 7,465,536 | B2 | 12/2008 | Gonzalez et al. |
| 7,524,673 | B2 | 4/2009 | Gonzalez et al. |
| 7,569,359 | B2 | 8/2009 | McDonnell et al. |
| 7,940,377 | B1 | 5/2011 | Schmitt et al. |
| 8,229,204 | B2 | 7/2012 | Wagner |
| 8,760,656 | B2 | 6/2014 | Matsumoto |
| 9,351,797 | B2 | 5/2016 | Bommarito et al. |
| 9,575,022 | B2 | 2/2017 | Bommarito et al. |
| 9,739,764 | B2 | 8/2017 | Lee et al. |
| 9,783,839 | B2 | 10/2017 | Philipak et al. |
| 9,885,664 | B2 | 2/2018 | Frieze |
| 10,002,276 | B2 | 6/2018 | Orati et al. |
| 10,027,878 | B2 | 7/2018 | Nakano et al. |
| 10,048,203 | B2 | 8/2018 | Rochette et al. |
| 2012/0196375 | A1 | 8/2012 | Granja et al. |
| 2019/0102876 | A1* | 4/2019 | Sanders ............... A61L 2/28 |
| 2020/0147254 | A1* | 5/2020 | Lombardía ........... A61L 9/015 |

FOREIGN PATENT DOCUMENTS

| | | | | |
|---|---|---|---|---|
| EP | 1 709 979 | A1 | 10/2006 | |
| JP | 2006-346136 | A | 12/2006 | |
| JP | 2009061012 | * | 3/2009 | ............ A61B 19/00 |

OTHER PUBLICATIONS

PCT Written Opinion of the International Searching Authority of International Application No. PCT/IB2020/052550 dated Jun. 30, 2020, 8 pages.

PCT International Search Report of International Application No. PCT/IB2020/052550 dated Jun. 30, 2020, 3 pages.

Catalog, "CDW Cleaning Indicator-Rev. 12", TERRAGENE, Jul. 31, 2017, Retrieved from the Internet: < URL:https:scu.com.tr/wp-content/uploads/2017/08/CDWA-Rev.12.pdf) p. 1, col. 3, lines 7-15, 53-60, figs. 2, 3; table 1.

Michelle J. Alfa, PhD, FCCM et al., "Comparison of Washer-Disinfector Cleaning Indicators: Impact of Temperature and Cleaning Cycle Parameters", American Journal of Infection Control, 42 (2014) pages e23-e26, 4 pages.

J.R. Hesp et al., "Thermostable adenylate kinase technology: a new process indicator and its use as a validation tool for the reprocessing of surgical instruments"; Journal of Hospital Infection (2010) 74, pp. 137-143, 7 pages.

P.G. Nugent et al., Application of rapid read-out cleaning indicators for improved process control in hospital sterile services departments Journal of Hospital Infection 84 (2013) pp. 59-65, 7 pages.

Ralph J. Basile, healthmark Industries Co. "Instructions for Use: TOSI", Sep. 7, 2017, 3 pages; https://www.hmark.com/tosi.php.

PCT International Preliminary Report on Patentability of PCT/IB2020/052550 dated Sep. 28, 2021, 9 pages.

STERIS Corporation, "Verifying your cleaning process, VERIFY All Clan Test Washer Indicator", 2 pages, https://www.steris.com/healthcare/products/sterility-assurance-and-monitoring/chemical-indicators/verify-all-clean-testwasher-indicator/, Date: Aug. 2012.

* cited by examiner

CLEANING INDICATOR AND METHOD OF USING SAME

CROSS-REFERENCE TO RELATED APPLICATIONS

The present application is a U.S. National Phase Application of International Application No. PCT/IB2020/052550, filed Mar. 19, 2020, which claims priority to U.S. Provisional Patent Application No. 62/822,179, filed Mar. 22, 2019. The entire contents of these applications are incorporated by reference herein in their entirety.

FIELD

The subject matter disclosed herein relates to a cleaning indicator that is used to determine if articles that are cleaned in a washing machine, such as an endoscope reprocessing system, are in fact clean to a necessary degree following operation of the washing machine.

BACKGROUND

It is sometimes necessary to determine the efficacy of a cleaning process. For example, before being subjected to sterilization, instruments used in a surgical procedure must be cleaned to remove soils such as blood, stool, or other body fluids that remain on them after use. Even new instruments must sometimes be cleaned to remove substances left on their surfaces during manufacture. As used herein, a "cleaning process" or "washing process" relates to washing of articles in a washing machine, which can be operated manually or automatically.

The effectiveness of a cleaning process can be verified by use of a cleaning indicator, which indicator can be one containing an active agent, such as a color changing chemical sensitive to a specific chemistry or physical condition such as temperature, and a carrier substrate (i.e., support system) for supporting the active agent. Effectiveness of a cleaning process is indicated by a change in the color of the active agent, which is then evaluated by an operator, for example by visual inspection, after the cleaning process is completed. Alternatively, the indicator can comprise a substrate having an image printed on it in an ink that is susceptible to being washed off the substrate by the cleaning process, and effectiveness of the cleaning process is evaluated by visual observation of the image to determine the completeness of its removal.

SUMMARY OF THE DISCLOSURE

One aspect of the present disclosure relates to a cleaning indicator comprising at least one substrate including an image side bearing at least one query image and at least one test soil covering at least a portion of the at least one query image. In an alternative embodiment, a cleaning indicator can comprise at least one substrate including an image side bearing at least one query image that is formed from a test soil.

This aspect of the present disclosure includes an article comprising such a cleaning indicator, and further comprising a holder that encompasses the cleaning indicator and includes passages of various shapes and sizes disposed proximate to the image side.

Another aspect of the present disclosure relates to a method for monitoring cleaning of articles comprising:

i. arranging in a washing machine system the articles and a cleaning indicator comprising at least one substrate including an image side bearing at least one query image and at least one test soil covering at least a portion of the at least one query image;

ii. commencing a washing cycle to wash the articles using the washing machine system to remove at least a portion of the at least one test soil to expose at least an exposed portion of the at least one query image;

iii. scanning the cleaning indicator using an imaging apparatus to detect the exposed portion of the at least one query image; and iv. determining, with a processor, that the exposed portion of the at least one query image matches the at least one query image; and v. stopping washing the articles.

Some embodiments of this aspect of the disclosure may further comprise measuring a starting reflectance or fluorescence of the blank image before step ii, and wherein the determining step includes determining that the exposed portion of the at least one query image provides a reflectance or fluorescence within 95% of the starting reflectance.

Another aspect of the present disclosure is embodied in a washing machine system comprising
- an enclosure containing a rack suitable for holding articles to be washed;
- a fluid handling system for conducting a wash cycle for washing and rinsing the articles;
- an imaging apparatus for gathering image data;
- a holder disposed in the enclosure proximate to the imaging apparatus, the holder configured to contain a cleaning indicator such that at least a portion of the cleaning indicator is visible to the imaging apparatus;
- a non-transitory storage medium containing reference-shape data;
- an electronic control configured to activate the washing cycle; and
- a processor configured to compare the image data to the reference-shape data and to signal to the electronic control to activate the washing cycle.

A further aspect of the present disclosure lies in a method for monitoring cleaning of articles comprising:

i. arranging in a washing machine system the articles and a cleaning indicator comprising a substrate bearing on an image side at least one query image formed from at least one test soil, and having a blank area of uncovered substrate to be interrogated by an imaging apparatus;

ii. commencing a washing cycle to wash the articles using the washing machine system to remove at least a portion of the at least one test soil to expose at least an exposed portion of the substrate;

iii. scanning the cleaning indicator using an imaging apparatus to image the area of the at least one query image, and to image the blank area by reflectance from or transmittance through the substrate; and iv. comparing, with a processor, the reflectance from or transmittance through the portion of the cleaning indicator that was covered by the test soil to the amount of reflectance from or transmittance through the blank area of the substrate; and v. if the reflectance from or transmittance through the area of the substrate initially covered by the test soil is within a clean criterion of the reflectance from or transmittance through the blank area, stopping washing the articles.

BRIEF DESCRIPTION OF THE DRAWINGS

The specification concludes with claims, which particularly point out and distinctly claim the subject matter described herein and so define the invention disclosed herein. The accompanying drawings, which are merely illustrative, and should not be considered as describing all embodiments or otherwise limiting the invention that is encompassed by the claims, are provided to assist in understanding the disclosed invention. In the drawings, like reference numerals identify the same elements.

MODES OF CARRYING OUT THE INVENTION

Figure 1A:
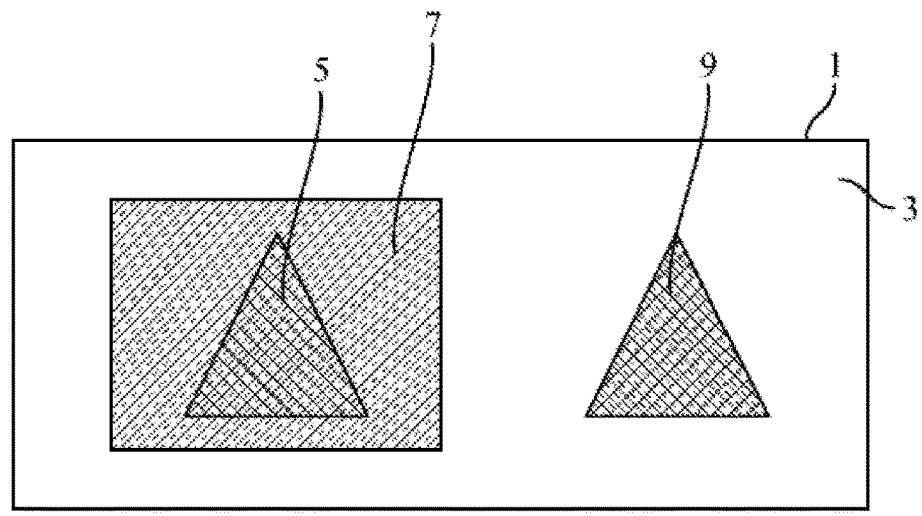
FIGS. 1A-1F depict various forms of the cleaning indicator according to the disclosure.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%.

Presently disclosed is a cleaning indicator that can be used to evaluate the efficacy of a cleaning process conducted in a washing machine. Such a cleaning process is one intended to remove various soils from articles, for example instruments or medical devices used in a surgical or other medical procedure, but unless otherwise stated, the articles to be washed are not so limited. In some embodiments, the washing machine works automatically; in relation to the present disclosure, particular automatic operations can be those with respect to ending the washing procedure (or "washing cycle") and unlocking of the machine. An automatic operation can also be one of starting and further controlling a washing procedure after manually pushing a "start" button by an operator of the washing machine.

Typically, cleaning indicators must be inspected manually, i.e., by visual evaluation of the indicator by one conducting a washing process, with the attendant problems of interruption of the cleaning process to confirm that it has been effective, and the subjectivity of the evaluation of efficacy of the cleaning process that has been conducted. The cleaning indicators presently disclosed can be used in such a fashion, but they also improve the existing technology by enabling automatic detection of the effectiveness of the washing process, without inspection of the cleaning indicator by a person. Thus, an ineffective cleaning process can be indicated to an operator as ineffective such that the process may be repeated or modified to make it effective, or can be continued without interruption to a point where it has become effective as indicated by the cleaning indicator. Continuing a cleaning process can include modifying the conditions of the cleaning process.

Another improvement to the existing technology concerns incorporating the cleaning indicator into a system that includes instrumentation for scanning the cleaning indicator and, if the cleaning indicator is not one that is recognized by the instrumentation as being genuine, or the cleaning indicator being used is of the wrong type (e.g. having a substrate requiring different cleaning conditions from those programmed into the washing machine to clean those articles being washed) the operator can be so informed, automatic operation of the washing machine can be stopped or prevented, or the washing machine may be locked.

In general, a cleaning indicator can be one comprising a substrate bearing (or showing) at least one query image on an image side and at least one test soil deposited on the image side of the substrate and covering at least a portion of the query image.

Such a cleaning indicator can be one wherein the query image comprises a first image portion and a second image portion, the first image portion being covered by a first test soil and the second image portion being covered by a second test soil different from the first test soil.

Such a cleaning indicator can be one further comprising a plurality of substrates, each substrate bearing at least one query image on an image side and at least one test soil deposited on the image side of the substrate and covering at least a portion of the query image.

A "query image" is one that is inspected, either visually by one conducting a washing process, or by devices included in a washing machine system, to determine whether the cleaning process has been effective to remove soils from articles being cleaned by the cleaning process. A query image can be in the form of a barcode or a QR code, a simple geometric shape (such as a circle or regular polygon—e.g. a triangle or a square) or a random but pre-determined and consistently drawn shape. A query image can be "filled", i.e. the area within the outline of the query image is printed, preferably with the same ink as used to print the outline, or can be presented only as an outline and having the substrate in the outlined area not covered by any ink. A query image can comprise a shape that includes a plurality of concave and convex portions. A query image can include a plurality of shapes that are not connected to one another.

A query image can be embossed on the substrate, leaving a depression in the substrate.

In some embodiments, the query image is completely covered by a soil intended to be removed by the washing process (a "test soil") and an effective washing process is one that removes all of the soil from the query image so that the complete query image is seen upon visual inspection by the operator, or the complete query image is detected by a scanning device that is part of a washing system using the cleaning indicator.

Test soils can be either actual body fluids—e.g. blood or urine, tissues, excrements or the like, or "proxy" soils, as are known in the art, such as a Chemdye®, or a fat or carbohydrate substance. Some examples of test soils are listed in ISO 15883, including: nigrosin, wheat flour, hens egg, *E. faecium*, blood, bovine hemoglobin, *P. aeruginosa* biofilm, bovine serum albumin, porcine mucin, bovine fibrinogen, glycerol, dehydrated hog mucin, horse serum, unbleached plain flour, and an aqueous safranine solution.

Test soils can comprise a mixture of two or more compositions or substances. In some embodiments, the test soil is applied to the substrate to cover the desired portion of the query image and dried to bind it to the cleaning indicator.

In some embodiments, a depression of an embossed query image is filled with the test soil.

In some embodiments, a portion of the query image is left uncovered by any test soil, and such an uncovered portion can be interrogated as a "blank" portion of the image that serves as a reference for reflectance or fluorescence measurement of a clean surface bearing the ink used to produce the query image. In some embodiments, the substrate is printed with both of at least one query image and a separate blank image, using the same ink. In such embodiments, a query image is covered with one or more test soils and the blank image is left uncovered by any soil.

Any material durable in the washing process in which the cleaning indicator is to be used might be used as a substrate. Preferably, the substrate is one that provides a rigid, or at least only slightly flexible, surface suitable for handling without flaking of the ink used to print the images on the substrate and preferably without flaking of the test soil applied over the query image. Suitable substrates include laminated paper, a plastic—for example, polycarbonate or polystyrene or polymethylmethacrylate, a glass, a metal, or a suitably stiff rubber. The substrate can be a laminated paper, a plastic, a rubber, a metal, a ceramic, a glass or a composite of any two or more of these. In some embodiments, the substrate is a material similar to the material used to manufacture a part or the whole of an article being cleaned in the washing process in which the cleaning indicator is used. For instance, a substrate might be made from the same rubber used to produce the tubing portions of an endoscope. A borosilicate or pyrex glass might be used as a substrate for a cleaning indicator for a process used to wash laboratory glassware.

A cleaning indicator as disclosed can also include a magnetic strip or RFID chip that can hold information relating to the indicator and integrating the handling of the cleaning indicator or its associated articles into a hospital or laboratory supply chain management system. Alternatively, such information can be encoded in a barcode or QR code as part of a blank image or a query image.

In some embodiments, the cleaning indicator includes a plurality of substrates, each underlying a query image, or a portion of one query image, that is covered with the test soil. For instance, a substrate comprising a section of glass, a section of rubber and a section of plastic can be overlaid by a single query image and the query image then covered by a test soil. (Transparent or translucent substrates might be underlaid by a query image so that the image shows through the substrate on an image side bearing a test soil.) In some of these embodiments, each substrate material can be covered, in whole or in part, by a different query image. In some embodiments, the query image can include blank portions that allow interrogation of each substrate uncovered by either soil or ink that can serve as a reference surface for measurements of fluorescence or reflectance of each substrate.

Such embodiments as above can be made by adhering each different substrate to an underlying sheet of a suitable material, such as a laminated paper, a plastic, a rubber, a metal, a ceramic, a glass or a composite of any two or more of these Additionally or alternatively, any query image can be covered by a plurality of test soils of different compositions.

In some embodiments, the test soil can be applied to the cleaning indicator in a shape, or in a shape and color, that can be detected prior to the start of the cleaning cycle, and if that shape (and/or color) does not match an image stored by a washing machine utilizing the cleaning indicator, then the machine is not started. In some embodiments, the test soil can be formed into a shape that is used as the query image. In such embodiments, an area of the substrate not covered by the test soil formed into the query image can be used as a blank image or as a measurement standard for determining that the test soil has been completely removed from the substrate. In such an embodiment, the criteria for deeming that the washing cycle has been successfully completed can be that the reflectance of a light beam from the area covered by the test soil or transmittance of a light beam through the area of the test soil (if the substrate is transparent or translucent) is the same as the reflectance or transmittance of a reference light beam from the blank area of the substrate.

The ink that is used to print the query image can be any ink known in the art to bind to the selected substrate and to remain bound to the substrate under the conditions of the washing process. For example, Platinum Carbon Black ink is a highly water resistant pigment-based ink; Diamine Registrar's Blue-black ink is a waterproof iron gall ink. In some embodiments, the ink used to print the query image can comprise a fluorophore, preferably one that remains bound to the cleaning indicator under the conditions of the washing process (for example, perylene is a water insoluble flurophore). In some such embodiments, the cleaning indicator also includes a blank image printed on the substrate(s) using the same ink as used to print the query image.

In some embodiments, the substrate of the cleaning indicator can be transparent to optical or ultraviolet wavelengths, and the query image can be detected as a shadow in a transmittance image. In some such embodiments, an unprinted part of the substrate can serve as a blank image or blank portion of a query image.

Referring to FIG. 1A, a cleaning indicator 1 is illustrated, having a substrate 3 bearing a query image 5 and a blank image 9, which may be created via a suitable process, such as a printing process. Query image 5 is covered by a layer of test soil 7. Additionally, test soil 7 may cover a portion of substrate 3.

Figure 1B:
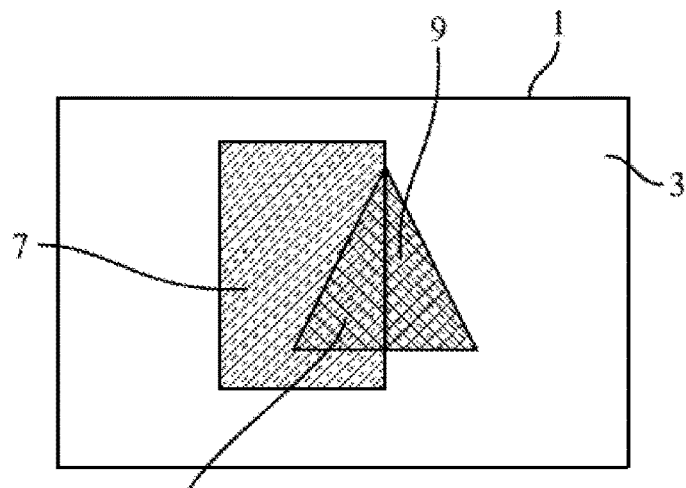

FIG. 1B shows a variant cleaning indicator 1, having a substrate 3 upon which is printed a query image 5, a portion of which is covered by a test soil 7, leaving a blank portion 9 uncovered by any test soil. Additionally, test soil 7 may cover a portion of substrate 3.

Figure 1C:
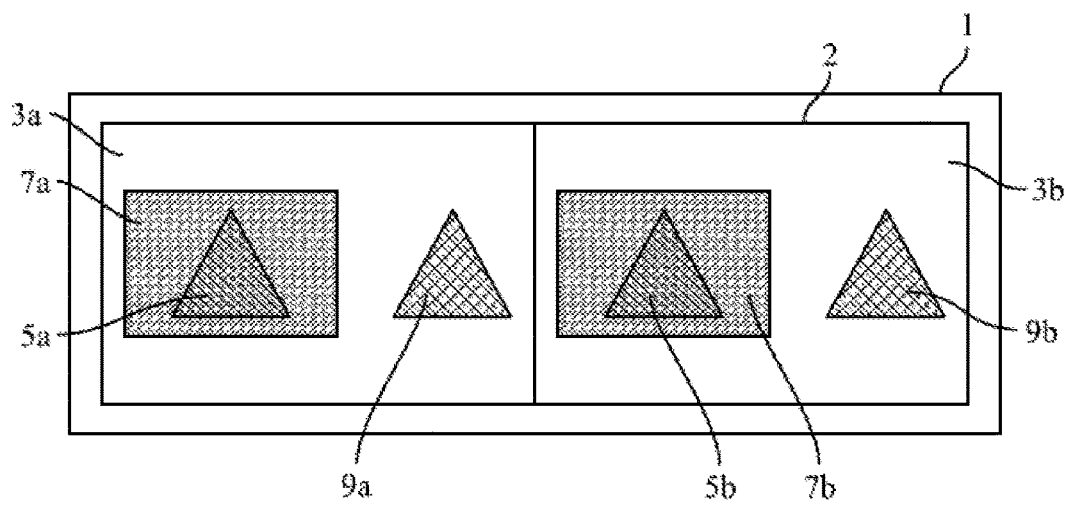

FIG. 1C shows another variant cleaning indicator 1, having a base layer 2 upon which are fixed two different substrates 3a and 3b. Each substrate has printed upon it a query image 5a and 5b and a blank image 9a and 9b, respectively. Each of the query images is covered with a test soil 7a and 7b, respectively. The test soils 7a and 7b can be the same or different. Additionally, test soils 7a and 7b may cover, respectively, a portion of substrate 3a and 3b.

Figure 1D:
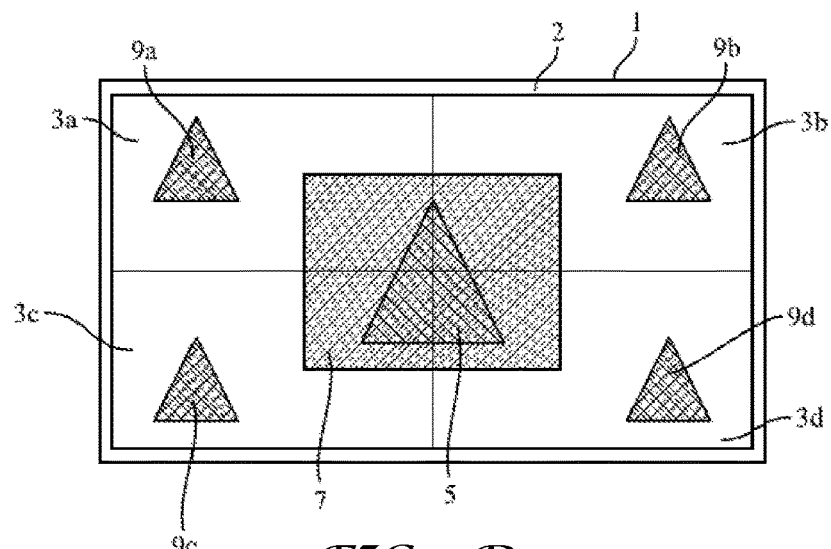

FIG. 1D illustrates another variant cleaning indicator 1, having a base layer 2 upon which is fixed four different substrates 3a, 3b, 3c, 3d. Each of the substrates has printed on it a blank image 9a, 9b, 9c, 9d, respectively, which preferably are all printed using the same ink. In this illustration all of the blank images are the same, but this need not be so. Each of the substrates is printed with a portion of the same query image 5, which crosses the boundary of each substrate. The query image is covered by a test soil 7, which may additionally cover a portion of any or all of substrates 3a, 3b, 3c, and 3d.

Figure 1E:
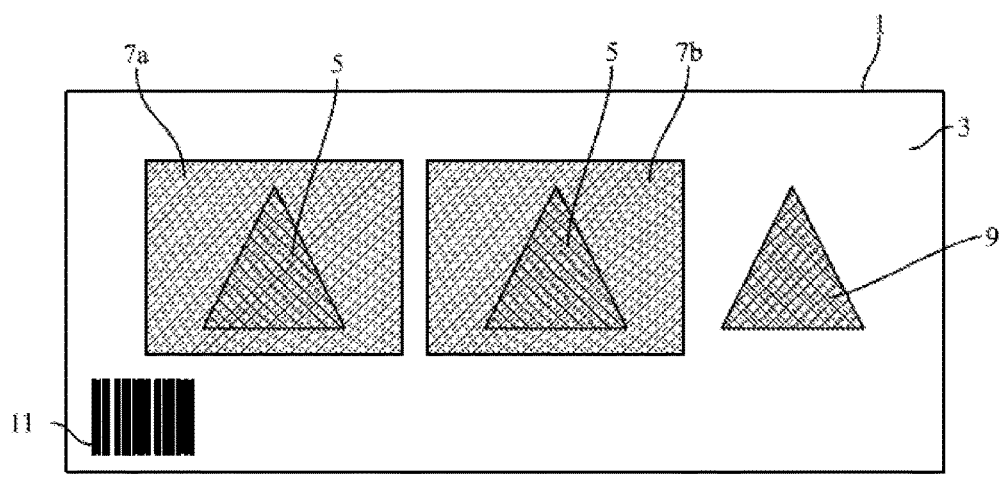

FIG. 1E illustrates another variant of a cleaning indicator 1, having a substrate 3 upon which are printed two query images 5 and a blank image 9. Each of the query images is covered by a different test soil 7a or 7b. Additionally, the test soils may cover a portion of substrate 3. Each of the query images and the blank image are shown as the same shape, but this need not be so. The cleaning indicator in this illustration also includes a bar code 11, which can be used to encode information about the nature of the articles being cleaned together with the cleaning indicator or otherwise encode data or instructions to interface with a supply chain management system of an enterprise.

Figure 1F:
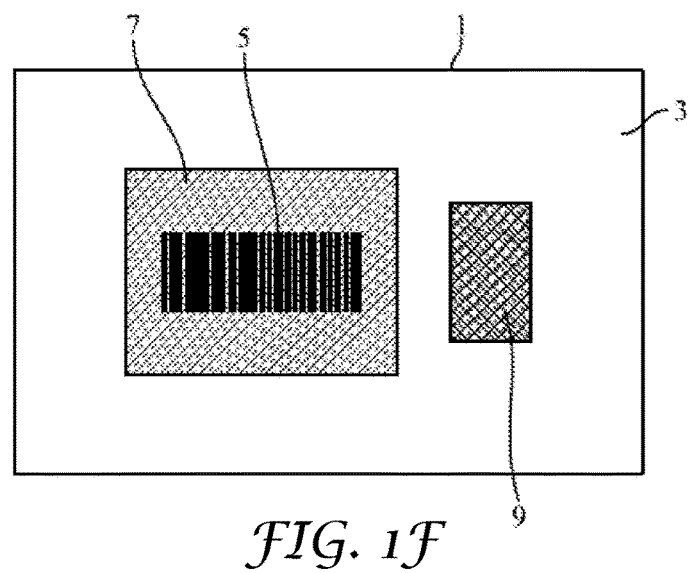

FIG. 1F illustrates another variant of a cleaning indicator 1, having a substrate 3 upon which is printed a query image 5 in the form of a bar code that is in turn covered by a test soil 7. An outlined, unprinted portion of the substrate 9 is preserved as a blank. In some alternatives, the blank can include a barcode not covered by any test soil.

Figure 2:
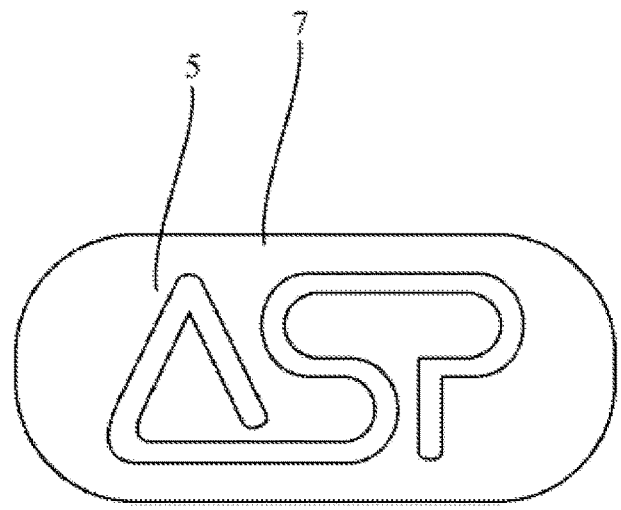
FIG. 2 depicts an illustration that can be used as a stored image for confirming the correct cleaning indicator is used.

FIG. 2 illustrates an image that might be used as a stored image to be used to confirm that a cleaning indicator used in a washing process is a correct cleaning indicator.

Figure 3:
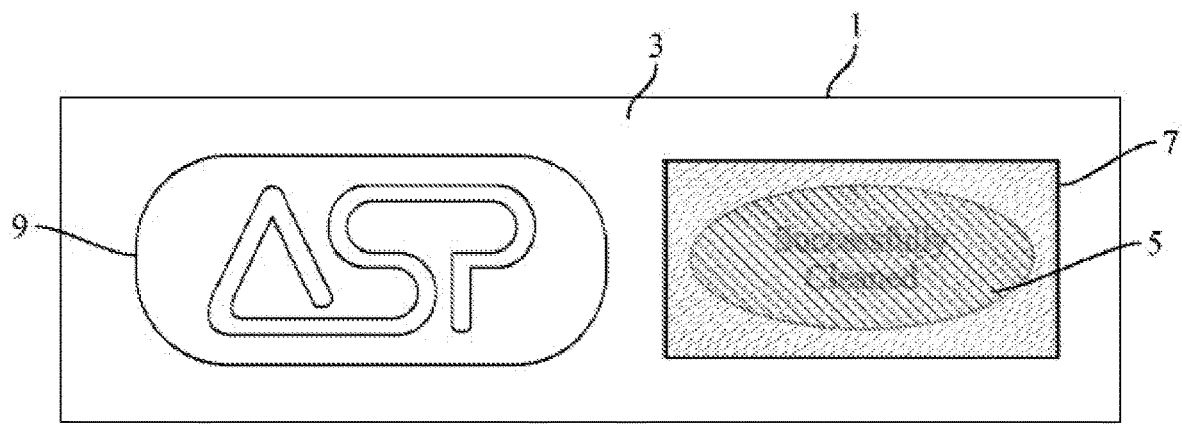
FIG. 3 illustrates a cleaning indicator including the illustration of FIG. 2 as a blank image and a second image as a query image.

FIG. 3 illustrates a variant cleaning indicator in which a substrate 1 has printed upon it a blank image 9 as illustrated in FIG. 2 and a query image 5 having a simple geometric shape surrounding a message. The query image 5 is covered by a test soil 7.

A cleaning indicator as disclosed herein can be used together with an article that serves to hold the cleaning indicator in a particular position, for example, such as a position in which the cleaning indicator may be scanned by a device that images the query image, or in some embodiments that images both the query image and a blank image. Such an article can be a holder that encompasses the cleaning indicator and includes at least one opening, such as passageways of various shape and size, through which the test soil surface of the cleaning indicator may be exposed to the cleaning environment inside a cleaning system or washing machine system, such that during a washing cycle, the cleaning indicator and particularly the test soil may be exposed to cleaning fluids. A holder for a cleaning indicator can be a simple frame holding two or more of the edges of the cleaning indicator, or might be configured as a "claw" that embraces the edges of a cleaning indicator.

The holding article will have at least one opening, such as the openings described in the preceding paragraph, or at least one alternative opening, through which light can pass from an image on the cleaning indicator to the scanning or imaging device (e.g. a digital camera or a bar-code or QR code reader). In some embodiments the holding article can also have at least one opening through which light from the scanning or imaging device can illuminate an image on the cleaning indicator.

Figure 6:
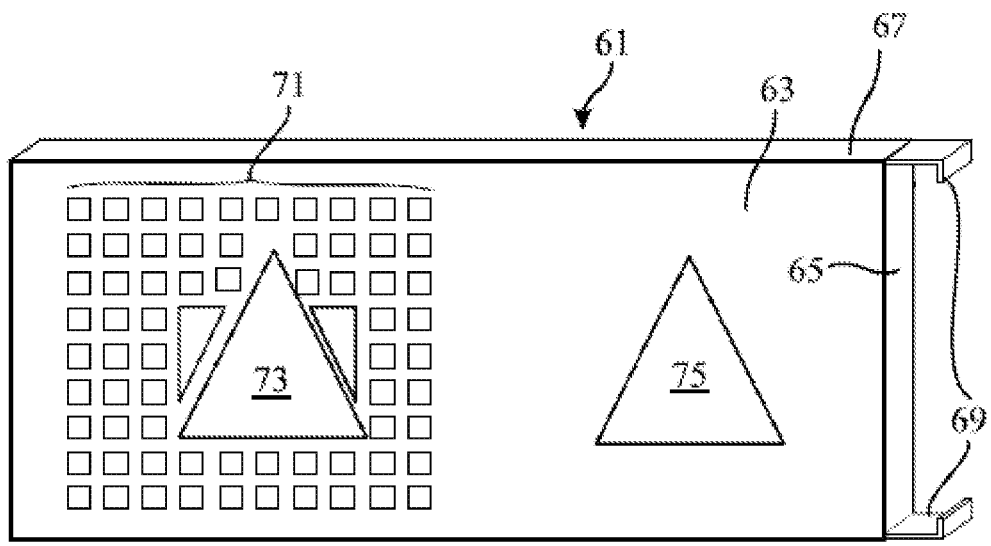
FIG. 6 shows an embodiment of a holder that can be used to hold a cleaning indicator in position for use in a washing machine system.

One embodiment of such a holder is illustrated in FIG. 6. The particular configuration shown is intended to be used with, for example, a cleaning indicator as shown in FIG. 1A. In FIG. 6, the holder 61 includes a frame 63 that encompasses the cleaning indicator (not shown) and has an opening 65 on one side and includes edges 67 and retainers 69 that are configured to hold the edges of a cleaning indicator inserted into the holder. The frame includes an opening 69 into which an indicator card can be inserted to be held by the frame. For example, the edges of the frame can have a u-shaped cross section such that the cleaning indicator can be slipped inside the frame and the edge of the cleaning indicator is held by the u-shaped cross section of the frame edge and the retainers. The frame is also perforated on its front side by a plurality of holes 71, which can be all the same, or of varying shape and size, through which the cleaning indicator card, and especially the test soil portion of the cleaning indicator, is exposed to the washing environment of the washing machine system. The frame is also perforated by an opening 73, of sufficient size and shape to allow illumination and imaging of the query image portion of the cleaning indicator. The frame is further perforated by an opening 75, of sufficient size and shape to allow illumination and imaging of the blank image portion of the cleaning indicator.

One or more cleaning indicators (and holders) as described above can be used in a washing processes implemented in a washing machine system. Such as system can be one that includes an enclosure holding within it apparatus suitable for holding articles to be washed, fluid handling systems for washing and rinsing articles to be washed, in some instances a system for venting aerosols and the like and for drying the articles after they have been washed, a holder that positions a cleaning indicator as disclosed herein to be imaged by an imaging apparatus for obtaining images of the cleaning indicator at one or more times in the washing process. The holder should also position the cleaning indicator in a manner that exposes the test soil surface and any blank image of the cleaning indicator to the cleaning process of the washing machine, and preferably exposes them to the cleaning environment of the washing machine. The holder might be accessible from the outside of the washing machine through an opening different from the one used to load articles into the machine.

The imaging apparatus can include a digital camera, which can be one configured to image a fluorescent emission or a reflected or transmitted light beam. In instances where a query and/or a blank image comprises a bar code or a QR code, the imaging apparatus can be a bar code or QR code scanner. The imaging apparatus can include hardware and software for illuminating an object to be imaged, for controlling illumination of an object to be imaged and for controlling exposure of an imaging sensor to the light coming from the object being imaged. Control of illumination and exposure can in some instances be by computational resources external to the imaging apparatus, or control of these can be divided between the imaging apparatus and external computational resources. (For example an external processor might control illumination and provide data to the imaging apparatus to set the appropriate exposure.) Fiber optic elements might convey light from a light acquiring element, such as a lens, to an imaging sensor. Such an arrangement might be used to dispose certain light gathering elements within the enclosure of washing machine and other imaging elements outside the enclosure of the washing machine. Also, multiple cleaning indicators might be disposed in different locations in the washing machine enclosure and convey images to a single imaging apparatus via such fiber optic elements.

The imaging apparatus can further comprise hardware and software elements, including but not limited to memory, a non-transitory storage medium (e.g., a solid state or disk hard drive) and processors (e.g., microprocessors) configured for running appropriate image acquisition and analysis software, for analyzing image data gathered by the imaging apparatus to determine whether a shape in the image corresponds to a shape stored in a memory module of the imaging apparatus, and for signaling to an electronic control in the washing machine whether a corresponding image has been detected or alternatively, that a different image has been detected. Alternatively, such image analysis hardware/software might be provided wholly or partly by computational resources external to the imaging apparatus and even external to the washing machine.

An image "corresponds to" or "matches" another image (e.g. a query image may correspond to a stored image) if the outlines of the shapes are the same or substantially the same when overlaid one upon the other. The criterion for correspondence can also include that a predetermined proportion of the length of the outline of the first image is found in the second image. This definition can be used with either line drawing images or filled shape images. In the instance of a filled shape image, a predetermined portion of the area of the filled image can also be used to define correspondence of two images. Preferably the proportion of the outline or filled shape detected matches at least 90%, more preferably 95%, or 99% of the complete outline or filled shape.

The criteria for correspondence or matching can additionally or alternatively include a threshold for a percentage of an initial reflectance, transmittance or fluorescence signal from a blank image or blank portion of a query image. Preferably, the percentage is set at least at 90%, more preferably 95% or 99% of the initial reflectance, transmittance or fluorescence, integrated over the entire image.

The washing machine system might further include computational resources that interface with material supply chain management systems in an enterprise. Such computational resources might collate an identification of the articles washed in a machine cycle with the data regarding the correspondence (or not) of the washed cleaning indicator to a "clean" indication after the cycle and perhaps also provide the current location of the articles as resident in the washing machine, as well as perhaps other data.

The washing machine system might also include electronic controls of its door locks or start switch that are configured to maintain the door locks in the "locked" position, and/or the start switch in the "off" position, in the event that the electronic control is signaled by the imaging apparatus that a query image corresponding to a stored image has not been received or if the control is signaled that a query image different from a stored image in its shape has been detected, or the control might be configured to maintain the door locks in the locked position until a signal is received that a "clean" indication has been detected.

Figure 4:
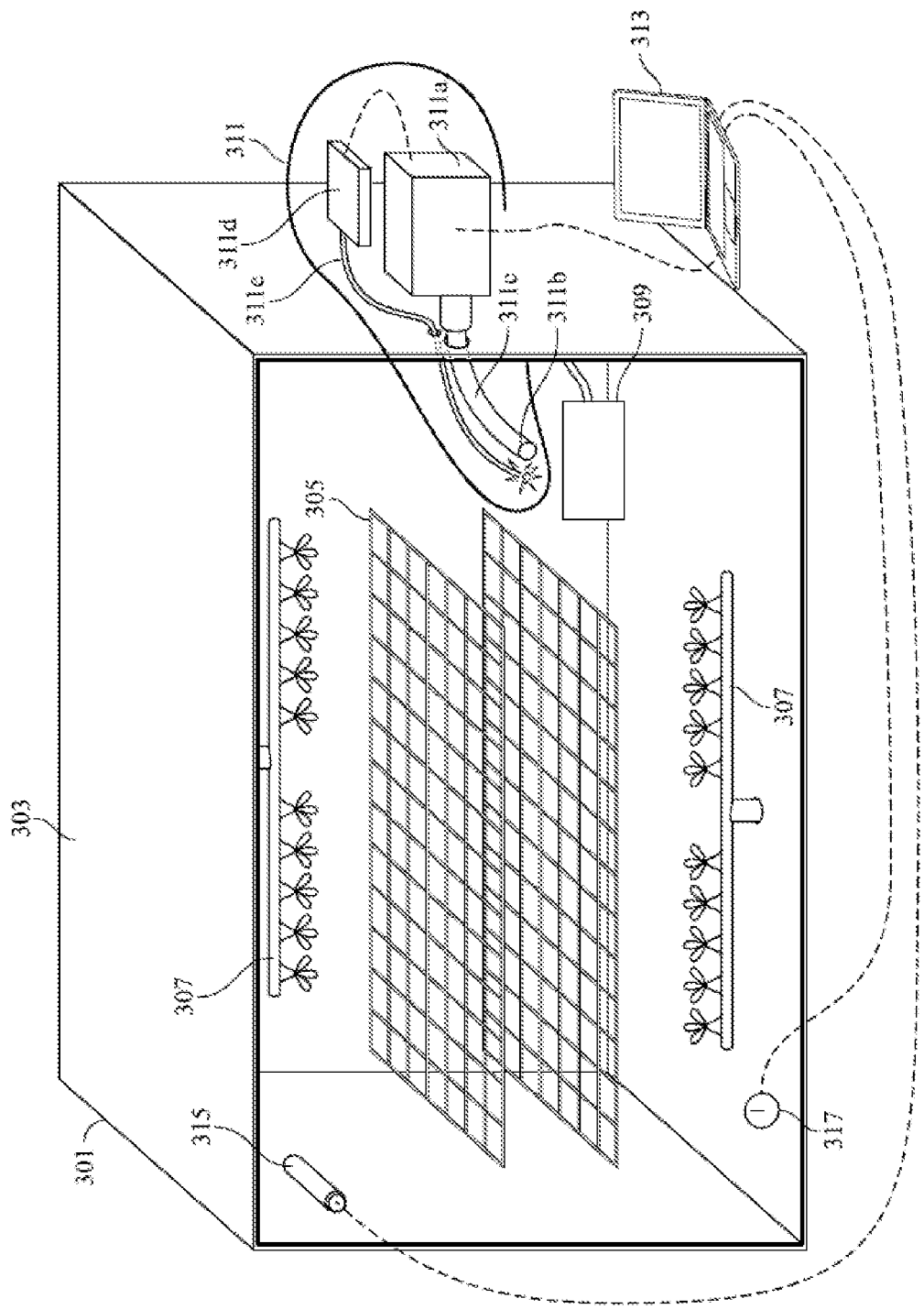
FIG. 4 shows an embodiment of a washing machine system in which a process as disclosed herein can be performed.

FIG. 4 illustrates one embodiment of such a washing machine system. The washing machine system 301 includes an enclosure 303, typically made from stainless steel, at least of a material resistant to corrosion, that encompasses the washing environment. Within the enclosure are one or more racks 305 upon which articles to be washed are arranged. The racks are also typically made from stainless steel, but might also be made from a plastic material. Also within the enclosure are the end parts (for example, spray heads mounted on a rotating arm) 307 of a fluid handling system that delivers water and other cleaning substances, such as detergents, rinse aids and the like, to the enclosure and distribute the cleaning substances and water and configured in a manner so as to expose the articles to them. The fluid handling system will include reservoirs for cleaning substances, valves, pumps, piping and tubing and the like for delivering water and the cleaning substances to the end parts in a manner known in the art.

One or more holders 309, which are configured to hold a cleaning indicator as otherwise described herein and to expose the cleaning indicator, at least the portion of it including the test soil-covered query image, and possibly the blank image or blank portion of the query image, to the washing environment, including the cleaning substances delivered by the end parts of the fluid handling system. The holders 309 are configured also to position the cleaning indicator, again including the test soil-covered query image, and possibly the blank image or blank portion of the query image, as might be applicable, to be imaged by an imaging system 311. In the illustrated embodiment the imaging system includes a digital camera 311a, that images the cleaning indicator through a lens 311b and, in some embodiments, a fiber optic element 311c. The imaging system illustrated also includes an illumination source 311d, that conveys light to illuminate the cleaning indicator, e.g., via a fiber optic element 311e.

Figure 7:
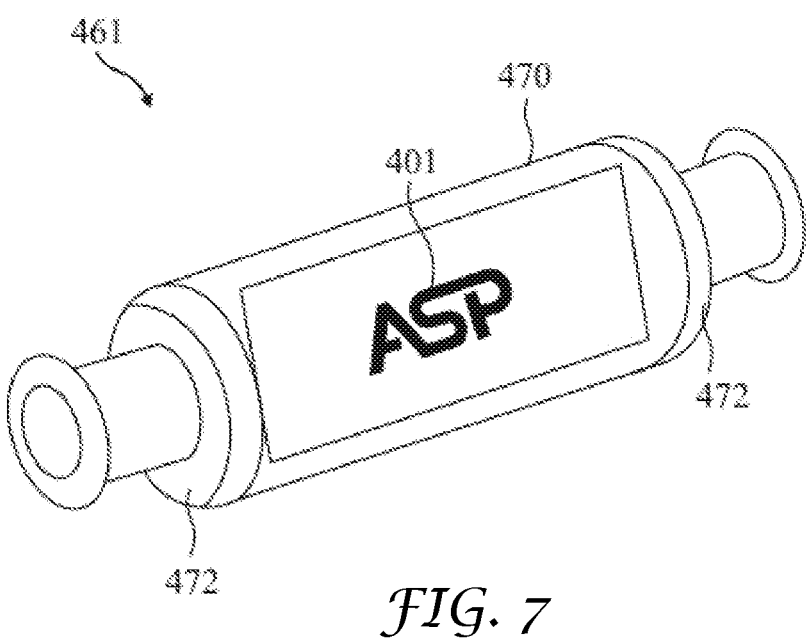
FIG. 7 shows another embodiment of a holder that can be used to hold a cleaning indicator and provide functionality for simulating flow through an endoscope lumen.

FIG. 7 reflects an embodiment of a holder or primary holder 461 for a cleaning indicator that provides functionality for simulating flow through an endoscope lumen. Holder 461 includes a body 470 (shown cylindrical) having at both ends, i.e., inlet and outlet, fluidic connectors 472 comprising, e.g., quick connectors, Luer fittings, etc. Fluidic connectors 472 may further include flow restrictors, e.g., a small-orifice device to reduce the volume flow rate of any fluid passing therethrough to simulate a flow rate through an endoscope lumen. As such, any of the cleaning indicators described above, shown as cleaning indicator 401 in FIG. 7, may be disposed within cylindrical body 470 of holder 461. One or more tubes connected to a source of a cleaning fluid may be connected to at least one of the fluidic connectors 472 to introduce the cleaning fluid into holder 461. Cylindrical body 470 is preferably made from a transparent material such that cleaning indicator 401 may be visualized and monitored as described herein.

Figure 8:
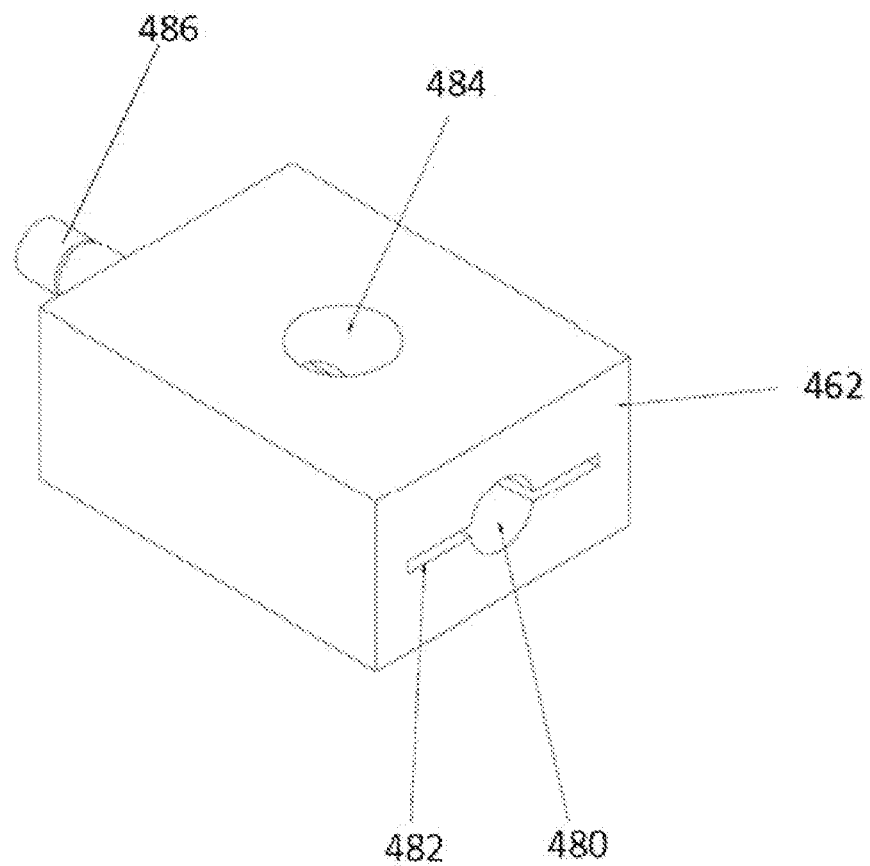
FIG. 8 shows an embodiment of a secondary holder that can be used to hold the holder of FIG. 7.

Holder or primary holder 461 may be used in conjunction with a secondary holder 462, shown in FIG. 8. Secondary holder 462 includes a port 480 for maintaining primary holder 461 therein. Secondary holder 462 may further include a slot 482 within which a cleaning indicator, e.g., any of the cleaning indicators described herein, may be disposed. Secondary holder 462 may additionally include an optical port 484 through which cleaning indicator 401 may be visualized within primary holder 461. Additionally, to provide further control of flow rate to simulate endoscope flow, secondary holder 462 may include a flow restrictor 486.

Flow restrictors incorporated directly in fluidic connectors 472 as well as flow restrictor 486 may function to restrict flow according to various mechanisms. For example, these flow restrictors may change a speed of the fluid by reducing a diameter of the flow path or may change a conductance of the fluid, e.g., by providing a plurality of empty volumes along the flow path such that the fluid must fill each volume before it can flow to the next volume, and ultimately to the cleaning indicator. Preferably, these flow restrictors, used singularly or in combinations, cause the flow properties (e.g., volume flow rate, mass flow rate, outlet pressure) of a cleaning liquid through primary holder 461 to be similar to the flow properties at a distal end of an endoscope lumen being cleaned in a washing machine system, such as system 301.

The article of claim 25, wherein the flow restrictor is configured is configured to change a conductance of the fluid.

The article of claim 25, wherein the flow restrictor comprises a plurality of empty volumes within the fluid path.

The imaging system conveys data to computational resources 313, which perform image-analysis to determine whether the "clean" criteria established for the washing machine system have been met. The results of the image analysis might also be used to determine whether a cleaning indicator appropriate for the washing procedure to be performed is present in the holder as described above. In the illustrated embodiment, the computational resources signal to a door locking mechanism 315 the result of image analysis in a manner that, if the "clean" criterion is not met, then the locking mechanism remains locked and the mechanism is unlocked if the "clean" criterion is met. In the illustrated embodiment, the computational resources also signal to a power switch 317 the result of analysis of a blank image of the cleaning indicator to remain "off" if the blank image does not correspond to an image stored in memory. However, if the blank image corresponds to the image stored in memory, the power switch may be activated to turn on washing machine system 301.

Computational resources 313 include a digital computer, e.g. a laptop or mobile device, or a networked computer, to control the operation of the washing machine system and its various components. Computational resources can employ one or more processors (e.g., microprocessors). Computational resources can also employ a non-transitory storage medium, such as random access memory (RAM), a hard-disk drive, or flash memory, which can store data, such as a manifest of articles being cleaned, control images, initial and time series fluorescence or transmittance data and the like, images constructed from data acquired by the imaging system, washing protocols including detergent nature and amount values, water temperature values and time values. Computational resources can further include software and/or logic for controlling a digital imaging system, which can include a fluorescence-based imaging system. Such software/logic can include instructions for controlling illumination, controlling a camera to acquire and produce an image, and to receive one or more acquired images from a camera. Computational resources can further include software and/or logic by which the microprocessor can numerically analyze image data. Computational resources can further include software and/or logic by which the microprocessor can compare a captured query image to a stored control image. Elements of camera control and image acquisition software/logic can be distributed between camera and digital computer devices. Computational resources can further include outputs to a display, for instance to show in some desired format a washing protocol that is run, and/or the results of comparison of the query and control images and/or fluorescence or transmittance data. Computational resources can also include software/logic for reporting results of a washing protocol (i.e. "successfully cleaned" or "not successfully cleaned", or the like), perhaps together with associated inventory information relating to articles being washed, to an inventory management system or the like implemented by a washing facility. Computational resources can also include software/logic for controlling various parts of the washing machine system, for example a locking system that opens a lock upon determination that a washing cycle has sufficiently cleaned articles being washed, or for example that controls a switch starting the wash cycle in a manner responsive to analysis of a control image.

Further disclosed herein are methods for monitoring cleaning of articles. Such methods are preferably performed in automated washing machines.

Figure 5:
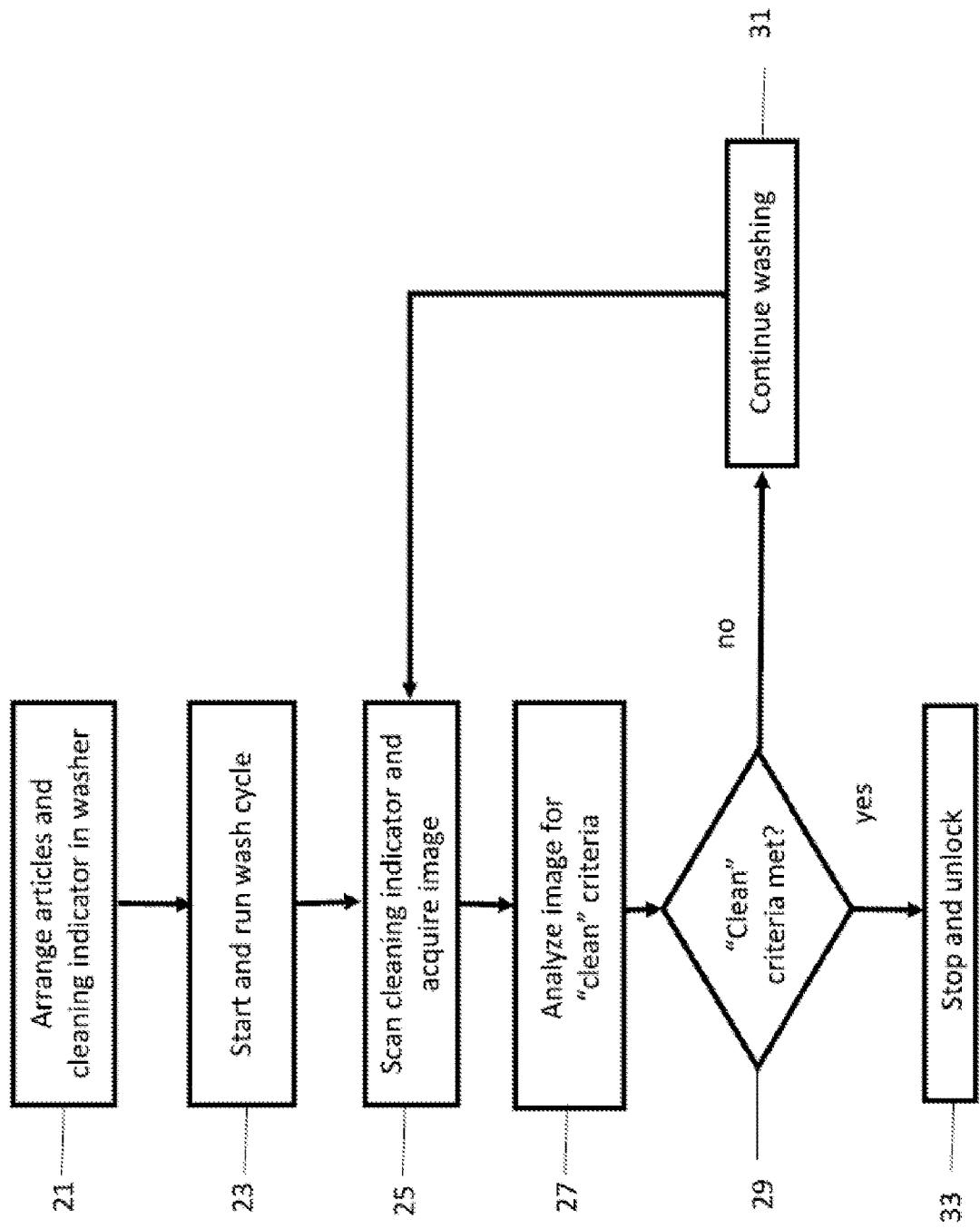
FIG. 5 shows a flow diagram of an embodiment of a method performed as disclosed herein.

FIG. 5 presents a flow diagram of an embodiment of a cleaning process as disclosed. At step 21, articles to be cleaned are arranged within a washing machine, and a cleaning indicator as described herein is also placed in the washing machine. The cleaning indicator is typically placed in a holder as described above to suitably position it to be exposed to the washing environment and to position it to be illuminated and viewed by a device for imaging the cleaning indicator. At step 23, a wash cycle is started and run. At step 25, the cleaning indicator is scanned by the imaging device to capture an image and at step 27 the captured image is analyzed to determine whether criteria that establish that the articles have been suitably cleaned have been met. Such criteria can be, for example, a sufficient reflectance, transmittance or fluorescence level is observed, or a certain proportion of the shape of the query image is detected. If the "clean" criteria are not met, then the washing cycle is continued at step 31 and the cycle of steps 25 and 27 and 29 are repeated until the "clean" criteria are met. Then, at step 33, the washing cycle is stopped and the articles are made available for removal from the washing machine.

A disclosed method can be one comprising:
arranging the articles and a cleaning indicator comprising a substrate bearing at least one query image on an image side and at least one test soil deposited on the image side of the substrate and covering at least a portion of the query image in a washing machine system;
running the washing machine system in a wash cycle;
scanning the cleaning indicator to detect the shape of the query image; and
stopping the wash cycle only after at least substantially the entire shape of the query image is detected.

A cleaning indicator as disclosed herein can be used in a manual method, in which the cleaning indicator is scanned by a hand-held reader, thereby enabling objective inspection of the indicator.

A method for monitoring cleaning of articles as disclosed herein can be one in which the cleaning indicator further comprises a blank image printed upon the image side using the same ink composition used to print the query image. Alternatively, such a method can be one in which the cleaning indicator includes a blank portion of the query image that is not covered by a test soil.

A disclosed method can be one that includes a step of measuring a starting reflectance, transmittance or fluorescence (luminosity) of a blank image, or of a blank portion of a query image, before the washing cycle of the washing machine system is started. Such a measurement of a starting reflectance, transmittance or starting fluorescence provides a reference measurement of a clean image that has no soil or residue from the cleaning process covering it. Thus, such a measurement provides a criterion for "clean" against which the progress of the cleaning process can be evaluated to determine automatically, i.e. without intervention of the operator of the washing machine if the washing process should be ended. Then, the washing process can be automatically continued until the reference criterion is met, at which time the washing process can be stopped. Alternatively, if the "clean criterion" is not met after the passage of a certain amount of time, an operator can intervene to change the washing conditions (perhaps including adding another cleaning indicator appropriate for the changed conditions) or the batch of washed articles can be flagged as inadequately cleaned and disposed of accordingly.

Such an automatically controlled washing process can be one including stopping the wash cycle only after the entire shape or substantially the entire shape of the query image is detected. Substantially the entire shape of the query image can be defined to include at least 90%, preferably at least 95%, or at least 99% of the complete outline of the query shape or of the complete filled area of the query shape (as might be applicable). In embodiments in which it is applicable, the automatically controlled washing process can be stopped when the query shape is detected at a reflectance or fluorescence of at least 90%, preferably at least 95% or at least 99%, of the starting reflectance or fluorescence integrated over the entire blank image.

In such a method, the query image can be scanned at the end of the washing cycle. In such an embodiment, the washing cycle can be re-started or continued if a deficient cleaning is detected, for instance by detecting a level or fluorescence or reflectance of the query image that is below the starting fluorescence or reflectance measured from the blank image (or blank portion of the query image), by some predetermined amount, or by failure to detect a complete shape of a query image.

An automatically controlled washing process can also be one in which the query image is scanned periodically or continuously during the washing cycle. In such an embodiment, the washing cycle can then be stopped when a reflectance or fluorescence value of the query image reaches a criterion value, or when a complete shape of a query image is detected, or a predetermined criterion of a combination of these variables is reached.

In some embodiments a blank image or the blank portion of a query image is scanned at the same time or in alternation with scanning of a corresponding query image (i.e. one printed with the same ink and on the same substrate as the blank) Such embodiments exhibit an advantage of being self-correcting, for example for fluctuations in reflectance or fluorescence measurements resulting from fluctuation in the intensity of the scanning or excitation beam, or due to scattering of the scanning or excitation beam or the signal beam by falling water drops or streams or fog occurring within the washing machine. In such embodiments, a time average of reflectance or fluorescence measurements in a manner known in the art are used to establish criterion for controlling the washing machine.

Embodiments of the presently disclosed method can include scanning of a blank image and preventing start of the wash cycle if the blank image detected by the scan does not correspond to a stored blank image. This embodiment can also be effected by using the shape and color of the test soil deposited over the query image. A blank image (or test soil image) would "correspond to" a stored blank image if the shape, and perhaps also the color, of the two images is the same within a predetermined criterion, or in an instance where the blank image is a bar-code or a QR code, if the scanned code and the stored code match. Such embodiments of disclosed methods have the advantage of precluding use of "third party" cleaning indicators that are not suitable for use in the washing machine system, or alerting an operator to mismatch of a cleaning indicator with a washing process it might not be suitable to evaluate. (For instance, when a cleaning indicator having a rubber substrate and stool as a test soil is inadvertently used in washing cycle for removing blood from glassware.)

Additionally or alternatively, such a method can be one comprising maintaining the washing machine system in a locked state if the query image detected by scanning it during or after the washing cycle does not correspond to a stored blank image or a stored query image.

A method for monitoring cleaning of articles can be one comprising:
i. arranging in a washing machine system the articles and a cleaning indicator comprising a substrate bearing on an image side at least one query image formed from at least one test soil, and having a blank area of uncovered substrate to be interrogated by an imaging apparatus;
ii. commencing a washing cycle to wash the articles using the washing machine system to remove at least a portion of the at least one test soil to expose at least an exposed portion of the substrate;
iii. scanning the cleaning indicator using an imaging apparatus to image the area of the at least one query image, and to image the blank area by reflectance from or transmittance through the substrate; and
iv. comparing, with a processor, the reflectance from or transmittance through the portion of the cleaning indicator that was covered by the test soil to the amount of reflectance from or transmittance through the blank area of the substrate; and
v. if the reflectance from or transmittance through the area of the substrate initially covered by the test soil is within a clean criterion of the reflectance from or transmittance through the blank area, stopping washing the articles.

In one embodiment, the stored blank or query image can be the image illustrated in FIG. 2. For example, a symbol or logo associated with a manufacturer of the cleaning indicator may be provided as the query image.

Devices and methods for scanning an image and determining its shape and color (i.e., "imaging") are considered known in the art (e.g., U.S. Application Publication 2011/0291830), as are devices for reading and evaluating barcodes or QR codes (e.g., U.S. Pat. Nos. 9,783,839 and 10,002,276; 9,739,764). Similarly, devices and methods for measuring the reflectance of a surface (e.g., U.S. Pat. No. 8,229,204) or for measuring fluorescence of a surface, both qualitatively and quantitatively, are also considered known in the art. Methods for qualitatively and quantitatively measuring fluorescence as a function of position in an image are also considered to be known in the art (e.g., U.S. Pat. No. 6,555,826). Quantitative methods including real-time correction of reflectance and fluorescence signals for fluctuation in scanning or excitation beam intensity and environmental scattering are also considered to be known in the art (e.g., U.S. Pat. Nos. 8,760,656 and 7,940,377).

Any of the examples or embodiments described herein may include various other features in addition to or in lieu of those described above. The teachings, expressions, embodiments, examples, etc., described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometries, materials, dimensions, ratios, steps, and the like discussed above are illustrative. Accordingly, the claims should not be limited to the specific details of structure and operation set forth in the written description and drawings.

I claim:

1. A cleaning indicator comprising:
   a base layer including a plurality of substrates each including an image side bearing at least a portion of a same query image; and
   at least one test soil comprising a soil and covering a portion of each substrate and at least the portion of the same query image for each substrate.

2. The cleaning indicator of claim 1, wherein the same query image comprises a first image portion covered by a first test soil and a second image portion covered by a second test soil different from the first test soil.

3. The cleaning indicator of claim 1 wherein at least one substrate comprises a laminated paper, a plastic, a rubber, a metal, a ceramic, a glass or a composite of any two or more of these.

4. The cleaning indicator of claim 1, wherein at least a portion of the same query image comprises an ink comprising a fluorophore.

5. The cleaning indicator of claim 1, wherein at least one image side further comprises a blank image printed from an ink also used to print at least a portion of the same query image.

6. The cleaning indicator of claim 1, wherein at least a portion of the same query image is not covered by any test soil.

7. The cleaning indicator of claim 1, wherein the at least one test soil is washable away.

8. The cleaning indicator of claim 1, wherein the at least one test soil is a proxy soil.

* * * * *